US009510686B2

(12) United States Patent
Abraham

(10) Patent No.: US 9,510,686 B2
(45) Date of Patent: Dec. 6, 2016

(54) ERGONOMIC SUPPORT APPARATUS AND METHOD FOR ASSISTING SLEEP

(75) Inventor: Oswald L. Abraham, Victoria (AU)

(73) Assignee: Cynthia R. Abraham, Victoria (AU)

( * ) Notice: Subject to any disclaimer, the term of this patent is extended or adjusted under 35 U.S.C. 154(b) by 666 days.

(21) Appl. No.: 12/918,769

(22) PCT Filed: Feb. 19, 2009

(86) PCT No.: PCT/AU2009/000179
§ 371 (c)(1),
(2), (4) Date: Nov. 22, 2010

(87) PCT Pub. No.: WO2009/103109
PCT Pub. Date: Aug. 27, 2009

(65) Prior Publication Data
US 2011/0056503 A1  Mar. 10, 2011

Related U.S. Application Data

(60) Provisional application No. 61/060,475, filed on Jun. 11, 2008.

(30) Foreign Application Priority Data

Feb. 22, 2008  (AU) ................................. 2008900852
Jan. 23, 2009  (AU) ................................. 2009900262

(51) Int. Cl.
*A61G 7/07*  (2006.01)
*A47C 20/02*  (2006.01)
(Continued)

(52) U.S. Cl.
CPC .............. *A47C 20/026* (2013.01); *A47G 9/10* (2013.01); *A61F 5/56* (2013.01); *A47G 9/109* (2013.01); *A61G 7/065* (2013.01); *A61G 7/07* (2013.01)

(58) Field of Classification Search
CPC ...... A61F 5/05883; A61F 5/56; A47G 9/1081; A47G 9/109; A47G 2009/1018; A47C 20/026; A61G 7/065; A61G 7/07
(Continued)

(56) References Cited

U.S. PATENT DOCUMENTS 2,182,861 A * 12/1939 Albert ............................... 5/722
2,782,427 A *  2/1957 Ericson ............................ 5/632
(Continued)

FOREIGN PATENT DOCUMENTS

CN  1638705 A  7/2005

OTHER PUBLICATIONS

Great Britain Intellectual Property Office Examination Report Under Section 18(3) dated Sep. 19, 2011 in Application GB1015685.9 (two pages).
(Continued)

*Primary Examiner* — Victoria J Hicks
*Assistant Examiner* — Kari Petrik
(74) *Attorney, Agent, or Firm* — McAndrews, Held & Malloy, Ltd.

(57) ABSTRACT

The present invention relates to the field of assisting sleep, including apparatus and methods for assisting sleep. In one form, the invention provides a postural support apparatus comprising a first supporting means (5) adapted to support the head of the user, a second supporting means (15) adapted to support the rib cage of the user, and a recess (3) intermediate the first supporting means (5) and the second supporting means (15), the recess (3) being adapted to accommodate at least part of an arm of the user, wherein the apparatus aligns the head and spine of the user such that the user's airways are kept open.

9 Claims, 6 Drawing Sheets

(51) Int. Cl.
*A47G 9/10* (2006.01)
*A61F 5/56* (2006.01)
*A61G 7/065* (2006.01)

(58) Field of Classification Search
USPC ..... 128/845, 848; 5/622, 630, 632, 636–640
See application file for complete search history.

(56) References Cited

U.S. PATENT DOCUMENTS

| | | | |
|---|---|---|---|
| 4,850,067 A | | 7/1989 | Latorre |
| 5,479,667 A | * | 1/1996 | Nelson et al. ............. 5/636 |
| 6,038,722 A | * | 3/2000 | Giori et al. ............... 5/709 |
| 6,105,187 A | * | 8/2000 | Gnjatovic ............ A47C 20/041 5/616 |
| 7,013,512 B1 | * | 3/2006 | Hsu ............................. 5/636 |
| 7,127,759 B2 | * | 10/2006 | Koops ................. A47G 9/10 5/636 |
| 7,536,741 B1 | * | 5/2009 | Schultz ................ A47C 27/146 5/733 |
| 2006/0253986 A1 | | 11/2006 | Rubio |
| 2008/0134437 A1 | * | 6/2008 | Small ....................... 5/632 |

OTHER PUBLICATIONS

The State Intellectual Property Office of the People's Republic of China, Notification of the First Office Action, Office Action, and Translation, in Application No. 200980113354.4, dated Dec. 12, 2011 (11 pages).
International Search Report of PCT/AU2009/000179 dated Apr. 23, 2009.
The State Intellectual Property Office of the People's Republic of China, Notification of the First Office Action, Office Action, and Translation, in Application No. 200980113354.4, dated Jun. 20, 2012 (14 pages).
Australian Government, Patent Examination Report No. 2, in Australian application No. 2009217220, dated Apr. 11, 2013. (3 pages).

* cited by examiner

ERGONOMIC SUPPORT APPARATUS AND METHOD FOR ASSISTING SLEEP

RELATED APPLICATIONS

This application is associated with Australian provisional patent application No. 2008900852 filed on 22 Feb. 2008, U.S. provisional patent application No. 61/060475 filed on 11 Jun. 2008, and Australian provisional patent application No. 2009900262 filed on 23 Jan. 2009 all filed in the name of Cynthia R Abraham and Oswald L Abraham, and the specifications thereof are incorporated herein by reference in their entirety and for all purposes.

FIELD OF INVENTION

The present invention relates to the field of assisting sleep, including apparatus and methods for assisting sleep.

In one form, the invention relates to a support apparatus adapted for use during sleep.

In another form, the invention relates generally to pillows. More particularly, the invention relates to a pillow designed to provide comfort and sleeping posture that generally ensures that the user maintains a clear airway.

While it will be convenient to hereinafter describe the invention in relation to promoting clear airways for the reduction of snoring and sleep apnea, particularly obstructive sleep apnea (OSA), it should be appreciated that the present invention is not so limited but extends to promoting clear airways in any subject irrespective of whether or not they suffer from a sleep disorder or other ailment.

BACKGROUND ART

Throughout this specification the use of the word "inventor" in singular form may be taken as reference to one (singular) inventor or more than one (plural) inventor of the present invention.

It is to be appreciated that any discussion of documents, devices, acts or knowledge in this specification is included to explain the context of the present invention. Further, the discussion throughout this specification comes about due to the realisation of the inventor and/or the identification of certain related art problems by the inventor. Moreover, any discussion of documents, devices, acts or knowledge in this specification is included to explain the context of the invention in terms of the inventor's knowledge and experience and, accordingly any such discussion should not be taken as an admission that any of the material forms a part of the prior art base or the common general knowledge in the relevant art in Australia or elsewhere on or before the priority date of the disclosure and claims herein.

Sleep is a state of rest in which a person or animal recuperates. Whilst the purpose of sleep is the subject of ongoing research, it is understood to play a role in bodily functions such as wound healing, immune system regeneration, hormone regulation, and muscular and skeletal rebuilding, as well as mental functions such as memory processing. Accordingly, poor sleep leads to problems in these important areas of human biological function.

Poor sleep may be the result of intrinsic factors (that is, arising internally) or extrinsic factors such as environmental conditions. In recent times there has been increasing interest and research in sleep disorders and their intrinsic and extrinsic causes.

Sleep apnea is a sleep disorder recognisable by its impact on the sleeper's breathing during sleep. A pause in breathing during sleep, called an apnea, disturbs the sleeper and results in a poor quality of sleep. A common form of sleep apnea is OSA, caused by obstruction of the sleeper's airways by the soft tissue of the mouth and throat. People suffering OSA or other serious sleep problems often unconsciously try to find ways to get comfortable during sleep. During sleep there is little or no conscious control over the body, thus if sufficient care is not taken prior to sleeping to ensure sufficient body comfort then snoring and sleep apnea can become serious problems.

Existing forms of treatment of OSA include Continuous Positive Airway Pressure (CPAP) devices, which act to hold the airways open, surgical techniques that remove and tighten tissue of the mouth and throat, and the use of various pillows that put the body on an incline.

Currently there are many pillows available in the global market for people with sleep apnea and snoring issues or problems. However these pillows may not work for all people as they typically only support the head and neck. This limitation in the design and construction arises due to the lack of a holistic approach to the body's need for posture and comfort. Posture is the manner in which we support our bodies when standing, sitting or lying down. When we are in a horizontal lying position if sufficient care is not taken to align the head, neck and spine, the airways may not be clear and problems such as sleep apnea and snoring may not be addressed.

Many prior art pillows attempt to improve the quality of sleep by trying to correctly position the head, or the head and neck in the supine position, or the foetal position. However, many prior art pillow designs do not go far enough technically to address sleep problems such as snoring or sleep apnea. In particular comfort and posture are not appropriately addressed, with the result that the throat muscles and the tongue relax during sleep. The tongue or uvula and soft tissues in the throat can fall back during sleep obstructing airways, causing the person to snore and/or temporally stop breathing.

Pillows of the prior art with soft filling such as, but not limited to, feathers or any other soft material may not work, because it is difficult to maintain a constant firmness or density, which is required for comfort and proper sleep. If such pillows only support the head and neck, they may also restrict the sleep positions, and may fail to address the problems of snoring and sleep apnea.

Pillows of the prior art that are contoured in a particular form or moulded in a certain way often have limited flexibility and do not allow free movement during sleep. They limit the positions the user may take resting and sleep, and this can cause discomfort. If such pillows only support the head and neck, they may not address the problems of snoring and sleep apnea.

For example, U.S. Pat. No. 6,671,907 B1 to Zuberi, defines a method for averting sleep apnea in a subject. The method includes the use of a convex shaped pillow with two openings at the bottom that allow one arm of the user to slide through. The user's head rests on the pillow head above the arm. Snoring is a problem associated with sleep apnea and the pillow of Zuberi does not seem to address that problem. There is also a real likelihood of the user's arm developing a cramp in response to the weight of the head and the pillow resting on the arm. Furthermore, the user may have difficulty turning from side to side to release the weight on their arm and this could lead to loss of sleep as the user tries to adjust to a new position. Like almost all pillows, the pillow described in the Zuberi patent is shaped as a single unit and its design and function limit the ease with which a user may adjust the position of their body before and during sleep.

U.S. Pat. No. 7,100,227 B2 to Frisbee describes an anti-snoring device having two parts—a top pillow and a bottom pillow. The bottom pillow is provided with a cavity or a head recess. The two parts operate as a single unit that provides support for a user's head only. However, the device of Frisbee does not support the rest of the user's body, that is, it does not orient the user's body relative to the rest of the body in a manner that overcomes snoring problems. Again, the device is shaped as a single unit and its design and function limit the ease with which a user may adjust the position of their body before and during sleep.

US design No. D529,327 S to Martin describes an isotonic pillow. It may comprise memory foam, thus providing an evenly distributed tension pillow. The pillow does provide some assistance for the head and neck area during the initial phases of sleep. It is during prolonged sleep that movement of the body is most likely to occur. In a deeper sleep condition it is difficult for the head and neck to confine its self to set contour of this pillow. Again a holistic approach is needed taking into consideration the head, neck shoulders and the lower end of the body for proper sleep.

U.S. Pat. Nos. 6,915,539 and 6,574,809, both to Rathbaun describes yet another form of pillow. However it is directed to the treatment of the skin care and wrinkles and does not teach anything with respect to snoring or sleep apnoea.

U.S. Pat. No. 2,700,779 to Tolkowsky discloses a therapeutic pillow designed to relieve muscular tension and strain to help with sleep. FIG. 3 illustrates the effect of a user sleeping on their side and indicates pressure on the users shoulder and hence pressure on the neck. FIG. 5 depicts a person sleeping straight on their back with a contour to support the head. This is position may not help a person with snoring or sleep apnea problems.

U.S. Pat. No. 5,708,998 to Torbik discloses a pillow that provides cervical support for people with different neck sizes. The only difference between this and a normal pillow is that this pillow has a cut out portion or recess in the middle allowing the head to fall back slightly allowing the neck to rest on the neck rolls. Specifically, Torbik describes a square pillow with a recess which is intentionally off centre. This provides a broad resting section at one end of the pillow for the neck of people of heavy build. The opposite end has a much narrower neck section to suit people who are of light build. Accordingly, the pillow can accommodate people of different builds simply by turning it around. However the pillow lacks a holistic approach and is directed solely to head and neck support.

U.S. Pat. No. 6,003,177 to Ferris, discloses a dove shaped pillow having a pair of supporting limbs that bend outwardly. It also includes a pair of neck, chin and jaw support limbs extending outwards. An opening between the two pairs of limbs allows breathing. The majority of people typically sleep on their sides or back and a few people sleep on their stomach. The pillow of Ferris does very little for people who sleep on their sides, or who sleep on their back. U.S. Pat. No. 6,226,818 to Rudlick discloses in the figures, two individual pillows. The pillows are required to be placed slightly apart to accommodate a user sleeping face down in the prone position. It may be convenient for short duration of sleep. Furthermore, in this prone position snoring may not be a problem, however users generally turn from a prone sleeping position to a side or supine sleeping position. With respect to the latter two positions these pillows do not help with snoring related problems.

U.S. Pat. No. 6,457,195 to Holste, describes a pillow that can be used for support of the neck of a user. One of the reasons for using a pillow of this design which wraps around the user's neck, is to assist a person with a snoring problem. Typically this type of neck pillow is also used in conjunction with a separate pillow to support the user's head. This type of pillow provides minimal support for the neck but lacks a holistic approach to user posture and can tend to interfere with normal sleep. Typically this type of neck support is used by travellers to who must spend many hours in an upright seated position, such as on an aeroplane.

U.S. Pat. No. 6,513,179 to Pan describes an essentially semi-circular device typically made from polymer foam, having an elongate internal hollow. Within the hollow is a firm piece of material with a recess in the middle. When a user rests their head on the semi-circle, the foam compresses and the user's head sinks into the recess. The firm piece of material provides good support for the neck. However, again the pillow provides support only for one part of the body and lacks a holistic approach to body support.

U.S. Pat. No. 6,539,568 to Lee, Jr. describes a device that displaces water in order to provide a comfortable support for a user's head and neck. Again, this prior art supports only the head and neck and lacks a holistic approach to body support. When the user enters the deeper levels of sleep and moves, the pillow will not assist them to maintain a constant comfortable position.

U.S. Pat. No. 4,748,702 to Sandler discloses an apparatus with a large contour section and an object in the middle of the pillow to prevent the back of the head directly resting on the middle of the pillow. As this design is rigid, limited in structure and function it can be difficult, during sleep or deep sleep for the user's body to conform to the requirements of this design.

U.S. Pat. No. 7,127,759 to Koops discloses an inflatable two part air pillow of wedge shape or having an inclined surface. One of the disadvantages of this design is that the user's body will need to adjust constantly during sleep, mostly because air pillows can become uncomfortable if the body sinks in too much or if it is too firm to allow the body to conform comfortably. Accordingly, the design and structure of the pillow has limited capacity to address problems such as snoring and sleep apnea.

U.S. Pat. No. 5,123,132 to Dixon discloses an anti-snoring pillow used to prevent or reduce the degree of blockage of a user's air passage and addresses the position of the head neck and shoulder. Like most pillows, this one only addresses the position of the head and neck to a small degree. The appropriate position of the shoulders, arms and lower body are not considered.

U.S. Pat. No. 3,521,310 to Greenawalt discloses a contour pillow designed to provide support to the user's neck. Contour pillows are formed in a specific, fixed shape and some shapes do not provide any more support than ordinary pillows. Specifically, once a user's head rests on a normal soft pillow, the weight of the head will automatically create a contour to cradle the head. The contour pillow of Greenawalt does provide some benefit for people who need help with snoring and sleep apnea problems, provided the contour suits their physique. However the pillow cannot be modified to the individual needs of the user.

U.S. Pat. No. 7,203,983 to Reeves et.al, discloses a pillow, particularly an orthopedic pillow designed to support the neck in a neutral spinal position. The pillow is limited in so far as it provides orthopedic cervical support for a user while they are sleeping on the back or side, but does not provide support for other parts of the spine. Like almost all pillows it is shaped as a single unit and limited in design and function with respect to body adjustment before and during sleep.

U.S. Pat. No. 5,644,809 to Olson, discloses a large contoured pillow with a rounded headrest. At the bottom end or base end it shows two openings in a 'V' shape to accommodate a user's left or right arm while sleeping. The arm may to slide into the opening until the head engages the headrest. One of the limitations of the structure of this pillow is that it restricts movement of the arm and shoulder when the user is sleeping on either side. Furthermore, a significant amount of adjustment of the user's body position is required when they change sides, which could result in loss of sleep or disturbed sleep.

U.S. Pat. No. 6,397,415 to Hsieh discloses an inflatable combination pillow consisting of a water chamber and an air chamber. The complete pillow addresses just the cervical section of the user's spine and is typically intended for orthopaedic use. Although it is restricted in structure, it would be difficult to make even minor adjustments as this may involve increasing or reducing water and air pressure.

U.S. Pat. No. 4,987,625 to Edelson discloses an adjustable personal support apparatus adapted to provide support to the user's body and head in both prone and supine positions. The benefits offered by the device flow from its generally angled shape to elevate the body. Edelson notes at column 2 lines 53 to 57 that the device may offer a benefit to users during sleep. Thus, the only contribution to mitigating closure of the user's airways during sleep is limited to the elevation of the user's upper body. In view of the foregoing, it would be desirable to provide a pillow that provides a sleeping posture that generally ensures that the airway of the user is clear and also provides comfort.

SUMMARY OF INVENTION

An object of the present invention is to provide an apparatus and method for adjusting the posture of a user such that the airways are kept open when they are lying asleep or resting.

A further object of the present invention is to alleviate at least one disadvantage associated with the related art.

It is an object of the embodiments described herein to overcome or alleviate at least one of the above noted drawbacks of related art systems or to at least provide a useful alternative to related art systems.

In a first aspect of embodiments described herein there is provided a method of supporting the posture of a user comprising the steps of:
  providing a first supporting means adapted to support the head of the user;
  providing a second supporting means adapted to support the rib cage of the user;
  providing a first recess intermediate the first and second supporting means, the recess being adapted to accommodate at least part of an arm of the user;
  wherein the head and spine of the user are aligned such that the user's airways are kept open.

In another aspect of embodiments described herein there is provided a postural support apparatus comprising:
  a first supporting means adapted to support the head of the user ;
  a second supporting means adapted to support the rib cage of the user;
  a first recess intermediate the first and second supporting means, the recess being adapted to accommodate at least part of an arm of the user,
  wherein in use the apparatus aligns the head and spine of the user such that the user's airways are kept open.

In a further aspect of embodiments described herein there is provided a postural support apparatus comprising:
  a first supporting means adapted to support the head of the user;
  a second supporting means adapted to support the rib cage of the user;
  a first recess intermediate the first and second supporting means, the recess being adapted to accommodate at least part of an arm of the user;
  wherein the apparatus is adaptable for aligning the head and spine of the user such that the user's airways are kept open.

In yet a further aspect of embodiments described herein there is provided a postural support means operatively associated with at least one of:
  a first head supporting means; and
  a second rib cage supporting means,
  wherein in use the first and second supporting means at least partly define a first recess adapted to accommodate at least part of an arm of a user,
  and wherein the head and spine of the user are aligned such that their airways are kept open.

In yet another further aspect of embodiments described herein there is provided a postural support means operatively associated with at least one of:
  a first head supporting means; and
  a second rib cage supporting means,
  wherein the first and second supporting means at least partly define a first recess adapted to accommodate at least part of an arm of a user,
  and wherein the head and spine of the user are aligned such that their airways are kept open.

In essence, the present invention stems from the realisation that it is possible to reduce blockage of airways and reduce airway restriction caused by compression of the torso, by correct alignment of the spine and head. The present invention further stems from the realisation that optimal alignment of the head and spine is dependent at least in part on positioning of the arms. This may concomitantly ameliorate conditions that interfere with sleep such as OSA and provide a preferable alternative to complicated and expensive therapies such as surgery or the use of positive pressure air masks during sleep. This pillow takes a holistic approach by providing posture and comfort for the body during sleep or rest.

Other aspects and preferred forms are disclosed in the specification and/or defined in the appended claims, forming a part of the description of the invention.

Advantages provided by the present invention comprise the following:
  A comparatively inexpensive and simple method for correcting posture and maintaining open airways,
  A simple apparatus that is readily manufactured from low cost materials,
  Comfort in addition to therapeutic effect.

Further scope of applicability of embodiments of the present invention will become apparent from the detailed description given hereinafter. However, it should be understood that the detailed description and specific examples, while indicating preferred embodiments of the invention, are given by way of illustration only, since various changes and modifications within the spirit and scope of the disclosure herein will become apparent to those skilled in the art from this detailed description.

BRIEF DESCRIPTION OF THE DRAWINGS

Further disclosure, objects, advantages and aspects of preferred and other embodiments of the present application may be better understood by those skilled in the relevant art by reference to the following description of embodiments taken in conjunction with the accompanying drawings, which are given by way of illustration only, and thus are not imitative of the disclosure herein, and in which.

LIST OF PARTS

Figure 1:
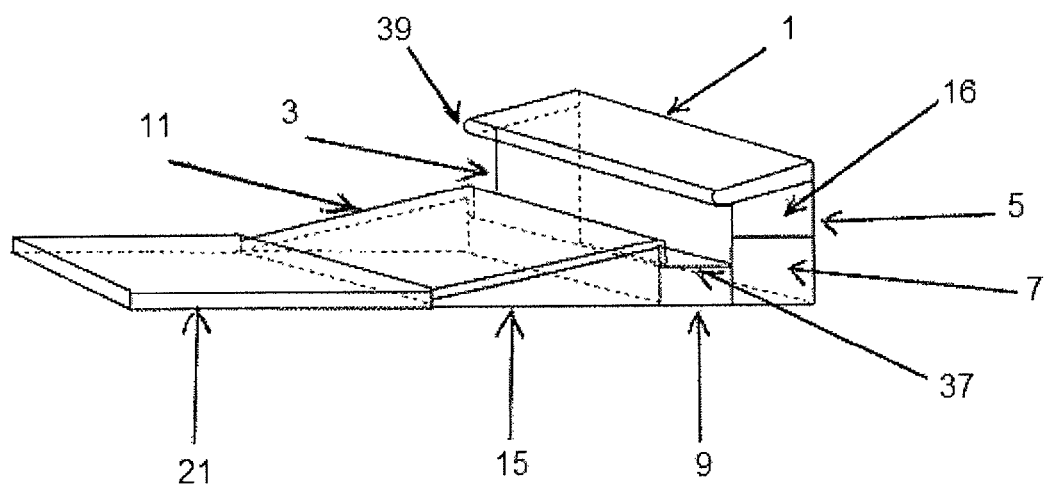
FIG. 1 illustrates, in perspective view, details of an ergonomic support apparatus in accordance with a preferred embodiment of the invention.

The following parts are referred to in the drawings and the detailed description of the drawings:

1. Headrest upper surface
3. Recess
5. Headrest
7. Headrest base
9. Bridge
10. Elevated front section of rib support 15
11. Upper surface of rib support 15
12. Top end of rib support 15
13. Lower end of rib support 15
15. Rib support
16. Headrest upper section
17. First insert
18. Second insert
21. Cushion
22. Lower end of cushion 21
23. Cushion folding point
24. Upper end of cushion 21
25. Interface between base 7 and headrest upper section 16
28. Interface between base 7 and bridge 9
29. Interface between bridge 9 and rib support 15
32. Bridge base
33. Rib support base
37. Top surface of bridge section 9
38. Recess for cushion 21
39. Overhang of headrest top section 1
41. Cover section for rib support 15
42. Cover section for bridge 9
43. Cover for headrest 5
44. Cover fastener
60. Cushion Air Inlet Valve
61. Rib support Air Inlet Valve
62. Headrest Air Inlet Valve
63. Headrest Air Exhaust Valve
64. Rib support Air Exhaust Valve
65. Extension Cushion Air Exhaust Valve
66. Bridge Air Exhaust Valve
67. Bridge Air Inlet Valve
68. Right bridge extension
69. Left bridge extension

DETAILED DESCRIPTION

FIG. 1 is a side perspective view of a pillow in accordance with an embodiment of the present invention. In the present embodiment, the pillow is designed to give full support and proper elevation for the upper body to generally ensure that the head, neck, arm, shoulder and spine section are aligned and have the proper posture during resting or sleeping. This is achieved by eliminating unwanted stress or pressure in the upper areas of the body.

Headrest

Figure 2:
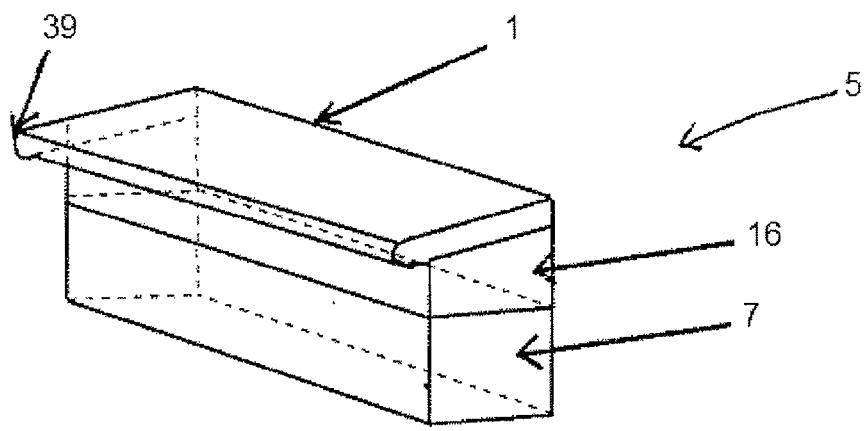
FIG. 2 illustrates, in perspective view, a portion of an ergonomic support apparatus in accordance with the embodiment shown in FIG. 1.

The elevated or 'top' end of the pillow comprises a headrest 5, which is typically removably attached to a further part of the pillow. FIG. 2 provides a perspective view of the headrest 5 and top surface 1 of the ergonomic support apparatus of FIG. 1. The headrest may be made from a suitable compressible material such as an expanded polymer, comprising latex or other foamed material. In a preferred embodiment a variety of headrests of differing densities are available, so that a person may interchange a soft headrest for a harder one to achieve a desired comfort level.

The headrest 5 has a higher elevation that the remaining sections of the pillow and is designed such that the user's head rests at an angle. The top surface 1 of headrest 5 slopes at an angle for this purpose. The angle of the headrest is generally chosen to ensure that the user's head is cushioned for comfort and to optimise posture. The headrest 5 is also sufficiently wide and long to allow free movement of the user's head when they change sleeping positions.

The top surface 1 of the headrest 5 is also typically formed from a layer of compressible material. As clearly shown in FIGS. 1 and 2, the top surface 1 overhangs the headrest and the edge of the overhang 39 may have a rounded edge 39 (as shown in FIGS. 1 to 4) or a square edge (as shown in FIG. 5). The overhang 39 fits neatly under the user's neck and together with the angle of the top surface 1 of the headrest 5, provides alignment, good posture, support and comfort for the user's neck, head, rib cage and spine during sleep.

In addition to the inclined top surface 1, the headrest 5 may comprise other sections which may be integral or detachable. For example, the upper section 16 may comprise a different density of foam to the base 7 of the headrest. Typically the base 7 comprises high density material while the upper section 16 comprises low density material, thus providing a comfortable combination of soft and firm material in the headrest 5.

Figure 8:
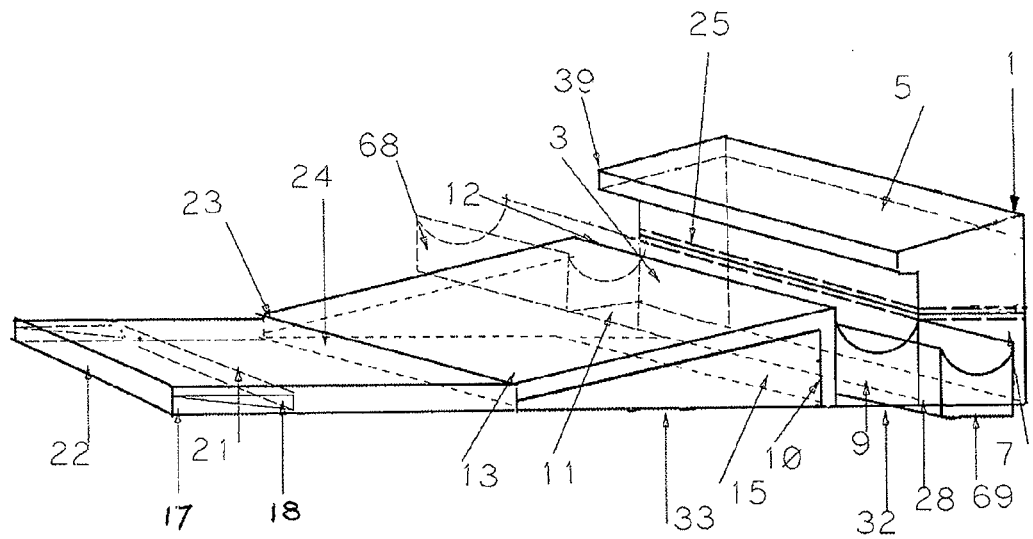
FIG. 8 illustrates, in perspective view, an ergonomic support apparatus in accordance with a further embodiment of the invention.
Figure 9:
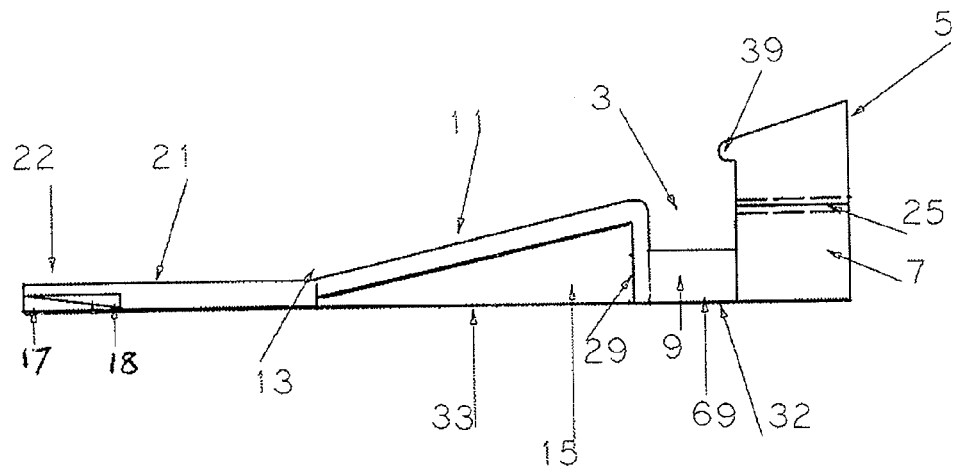
FIG. 9 illustrates, in right side view, an ergonomic support apparatus in accordance with the alternative embodiment shown in FIG. 8.
Figure 10:
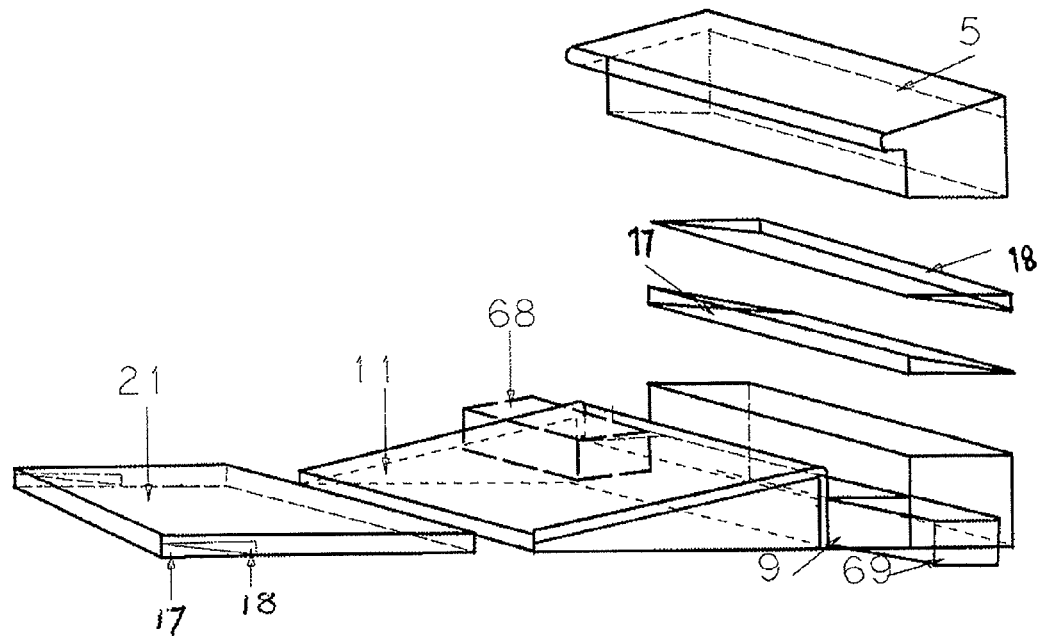
FIG. 10 illustrates, in exploded perspective view, an ergonomic support apparatus in accordance with the alternative embodiment shown in FIG. 7.

In a preferred embodiment the elevation and angle of the inclined upper surface 1 of the headrest 5 may be readily adjusted. For example, as depicted in FIGS. 9 and 10, the headrest base 7 may be detachable from the upper section 16 at interface 25. One or more additional inserts 17, 18 can be located between headrest base 7 and the upper section to provide additional height, and/or a forward or backward incline as required for comfort and support. The inserts may be of any convenient shape, but typically the inserts 17, 18 are wedge shaped as shown in FIGS. 7 to 11. In the embodiment depicted in the drawings, the pillow comprises two inserts. While the pillow can be provided with any convenient number of additional inserts in practical terms it would not be necessary, or comfortable, to raise the headrest by more than 10 mm. The use of two inserts will typically provide the headrest with a shape and angle that suits the large majority of users.

Figure 11:
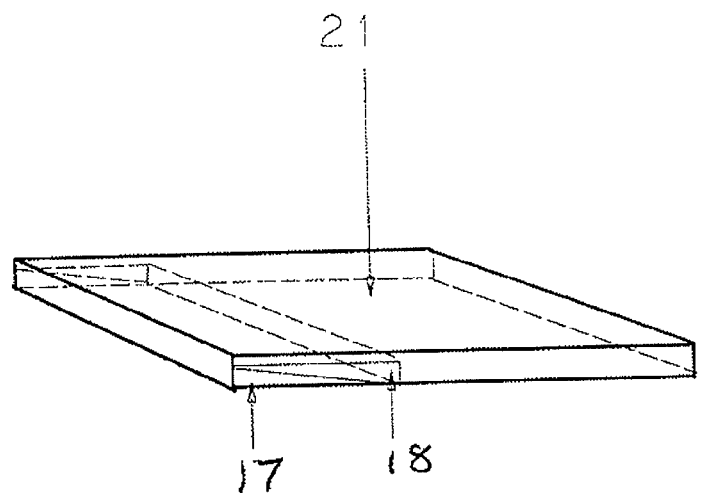
FIG. 11 illustrates, in perspective view, a portion of the ergonomic support apparatus in accordance with the embodiment shown in FIG. 7.

When not required, or not in use, the additional wedge inserts may be stored, for example, in the additional cushion 21 as shown in FIGS. 9, 10 and 11.

Recess

The pillow further comprises a recess 3 which is an important part of the pillow. The recess 3 has an opening to provide access for the user's arms and is configured to provide sufficient space for relatively free movement of the user's arm and shoulder while they are sleeping. Either arm may be received in the recess 3 which is configured to minimize any stress or weight to the arm or shoulder during sleep.

The recess 3 may be in the form of a channel of generally rectangular cross section (as shown in FIGS. 1 to 4) however, the recess may be configured in various other different ways. For example, without limitation, the part 37 of the bridge on which the user's arm and/or shoulder rests may be of generally hemi-circular shape (as shown in FIG. 5). The function of the pillow is the same irrespective of the configuration of the recess. Sleeping positions vary widely and some users may prefer to fold or tuck their hand between the headrest and the side of their face, while others may prefer to stretch the arm during sleep. The pillow allows for these, and any other positions the user may take during sleep. The recess is defined by the headrest 5, a bridge 9 and a generally wedge shaped rib support 15 having to an inclined upper surface 11. In use, the user's arm and at least part of their shoulder may rest on different surfaces of recess 3 depending on the position of the arm, for example, without limitation, the surface 37 of the bridge 9 or against part of the headrest 5 or rib support 15.

Bridge

The bridge 9 provides stability and strength to the pillow and holds the headrest 5 and rib support 15 in the correct position relative to each other. Typically the bridge 9 is made from expanded polymer material such as expanded high density polymer or a latex material and typically provides stability and strength. The upper surface 37 may be flat (as shown in FIGS. 1 to 4) or concave (as shown in FIG. 5) or any other convenient shape.

Figure 7:
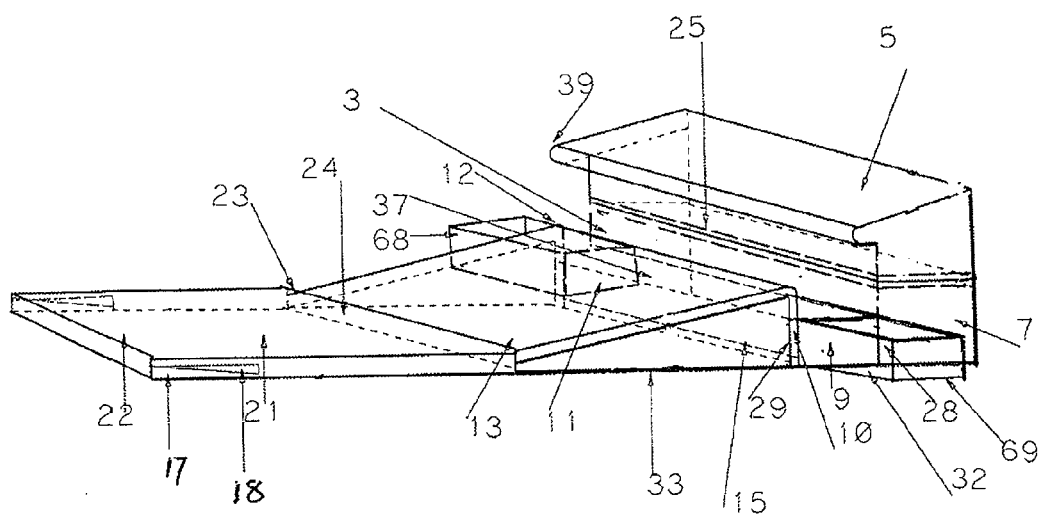
FIG. 7 illustrates, in perspective view, an ergonomic support apparatus in accordance with a further embodiment of the invention.

In a further embodiment the pillow may comprise bridge extensions 68, 69 as depicted in FIG. 7. The extensions 68, 69 project outwards from either side of the bridge 9 to provide additional support and comfort to the user's arms when they are sleeping on their left or right side. The upper surface of the extensions 68, 69 are typically planar, as depicted in FIG. 7, or concave as depicted in FIG. 8. The extensions 68, 69 may be integral or detachable from the bridge 9. Preferably the extensions can be stored in the recess 3 when not in use. For example, when the extensions are integral with the bridge 9, the extensions may be hingedly attached, such that they can be folded over and located on top of the bridge 9.

Rib Support

During rest or sleep, the rib support 15 supports the bulk of the user's weight inclined upper surface 11. In use the intermediate section 15 extends from the user's armpit to the lower section of their ribcage. It thus supports the user's body in a slightly upward angle from the end of the spine, through the rib cage, to the shoulder and arm. Typically the angle of inclined upper surface 11 is less than the angle on the top section 1 of the headrest 5. The difference in elevation and angle is provided to compensate for natural curvature from the shoulder to the neck while sleeping on either side. Typically the inclined upper surface 11 and the rib support 15 comprise expanded polymer of a density appropriate for supporting the weight of the user. For example, higher density material may be used for users with heavier body structure. The headrest 5, rib support 15, bridge 9 and cushion 21 may be of different densities or material. Furthermore the density within each of these components may be varied. The purpose of using varying densities is to optimise the user's rest or sleep position.

Cushion

Figure 6:
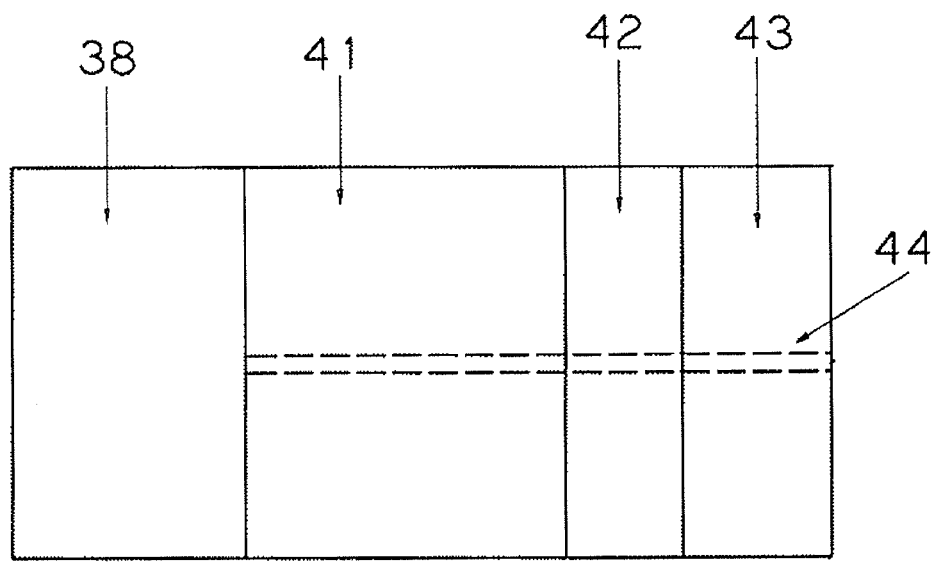
FIG. 6 illustrates, in top view, a cover for an ergonomic support apparatus in accordance with the embodiment shown in FIG. 1.

An optional cushion 21 may be used to extend the pillow and provide continuity, alignment, and support during sleep. Typically the cushion 21 is made of expanded polymer or latex. The cushion 21 may be of any convenient width and length. For example the cushion 21 may be the same length as the rib support 15. Alternatively the cushion 21 may be half to three quarters of the width and/or length of the rib support 15. Typically the cushion 21 is about the same thickness as the rib support 15 at their interface. With reference to this interface, the cushion 21 may be integral with, or alternatively removably attached to the rib support 15. The cushion 21 may angle up slightly from a lower end 22 to an upper end 24. A cushion folding point 23 adjacent the upper end 24 enables the cushion 21 to be folded over onto inclined upper surface 11 if the user does not want to use cushion 21, for example, during transport or storage. Alternatively the cushion 21 may be slid securely into an end pocket 38 of a cover (as shown in FIG. 6).

In use, the headrest base 7, bridge base 32, base of the intermediate portion 33 and cushion 21 rest on the surface on which the user is resting or sleeping. The surface may be for example, without limitation, a bed or floor.

Figure 3:
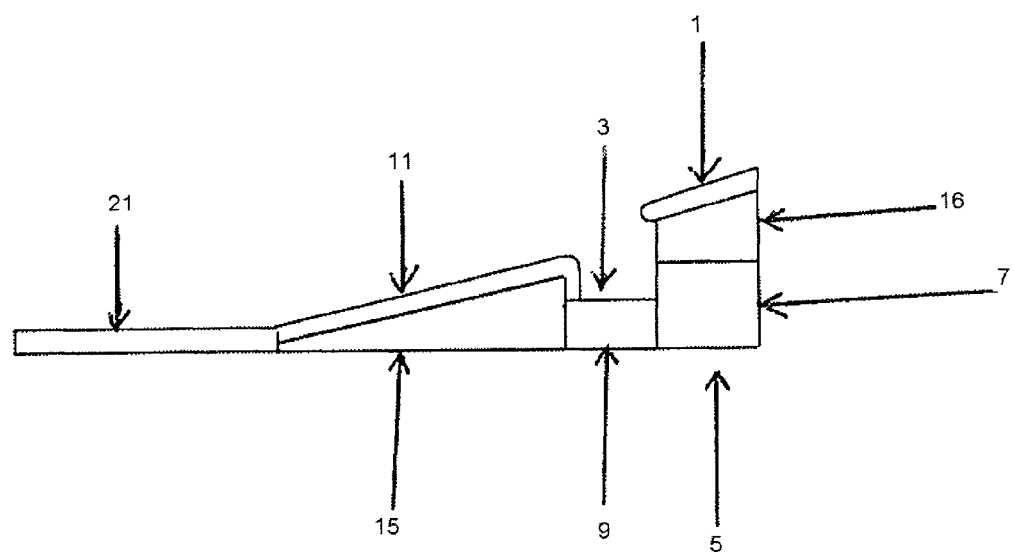
FIG. 3 illustrates, in right side view, an ergonomic support apparatus in accordance with the embodiment shown in FIG. 1.

FIG. 3 is a right side view of an exemplary pillow, according to an embodiment of the present invention. In this view the headrest 5, the upper surface of the headrest 1, the bridge section 9 and the inclined upper surface 11 of the generally wedge shaped rib support 15 and the cushion 21 can be clearly seen. The recess 3 is defined by the headrest 5, bridge section 9 and rib support 15.

One or more of these sections of the pillow may be integral. For example, they may be glued or otherwise permanently connected where they form an interface. Alternatively one or more of the sections may be removably attached (ie detachable). For example, sections may be joined by a releasable fastener such as hook and eye material sold under the trade mark 'Velcro'.

Figure 4:
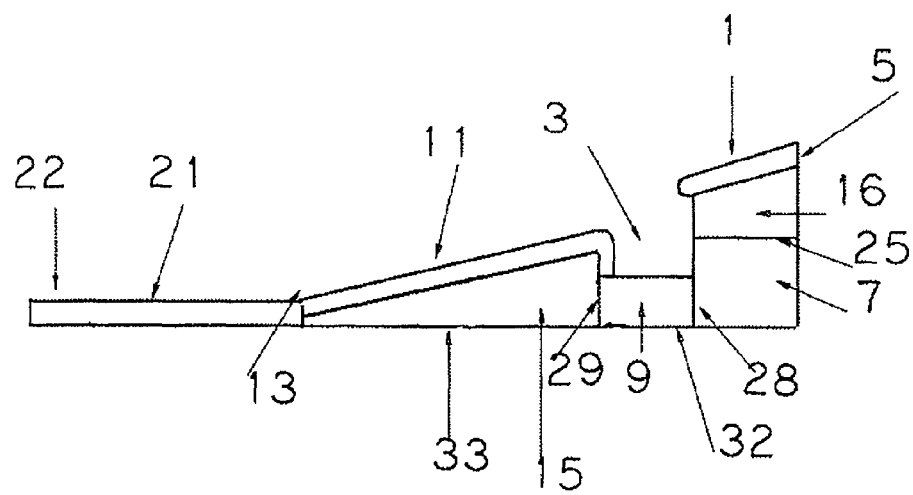
FIG. 4 illustrates, a more detailed right side view of an ergonomic support apparatus in accordance with the embodiment shown in FIG. 1.
Figure 5:
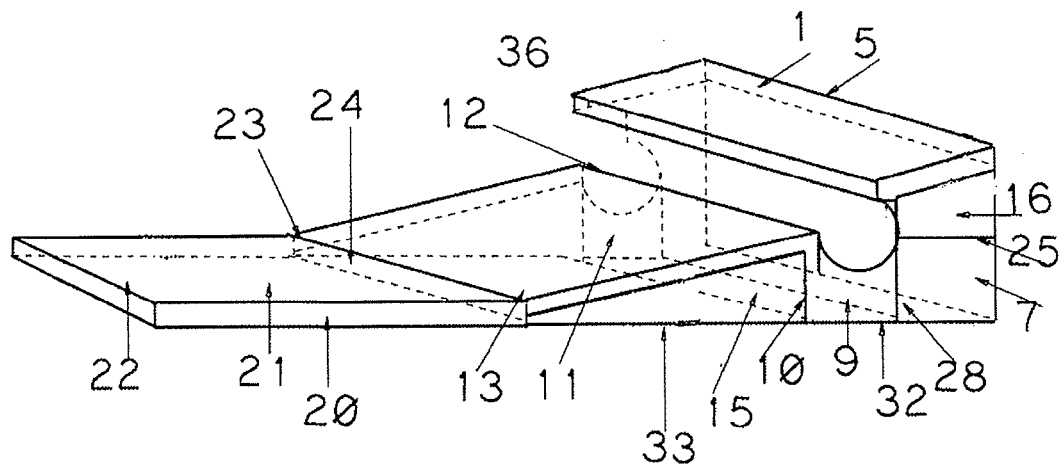
FIG. 5 illustrates, in perspective view, an ergonomic support apparatus in accordance with an alternative embodiment of the invention.

FIG. 4 is a more detailed right side view of an exemplary pillow, according to an embodiment of the present invention. In this view the headrest 5, the upper surface 1 of the headrest 5, the bridge section 9 and the inclined upper surface 11 of the generally wedge shaped rib support 15 and the cushion 21. The recess 3 is defined by the headrest 5, bridge section 9 and rib support 15.

The base 7 and upper section 16 of the headrest 5 may be integral or detachably fastened at their interface 25.

Similarly, the base 7 and bridge 9 may be integral or detachably fastened at their interface 28.

Similarly the bridge 9 and rib support 15 may be integral or detachably fastened at their interface 29.

Cover

Referring to FIG. 6, the pillow may comprise a cover made from any suitable material for comfort of the user and for protection of the pillow. Preferably the cover is made of a material that provides added comfort for the user. Furthermore, it is preferable that the cover material grips any surface on which it rests to avoid slipping or sliding of the pillow. The cover is typically designed to fit all of the sections and to conform to the contours of the pillow. The cover comprises a section 43 for enclosing the headrest 5 of the pillow, a section 42 for enclosing the bridge 9 of the pillow, a section 41 for enclosing the rib support 15 and a section 38 for enclosing the cushion 21. Each section 38, 41, 42 and 43 may be integral with one or both adjacent sections. For example, each section may comprise a separate pocket for enclosing a part of the pillow, or the sections taken together may constitute a single pocket for enclosing the entire pillow. When the cover comprises separate sections, each section 38, 41, 42 and 43 may be detachable from one or both adjacent sections. For example, in a preferred embodiment section 38 is in the form of a discrete pocket solely for receiving the cushion 21.

In one embodiment the cover may comprise a single fastener 44, such as a strip of Velcro™ or a zipper that can be fastened and unfastened for the purpose of inserting or removing the pillow from the cover. Alternatively, one or more sections 38, 41, 42 and 43 may have a dedicated fastener.

Construction

The pillow of the present invention may be readily constructed by any convenient means known to the person skilled in the art. For example the embodiments of the pillow shown by way of example in FIGS. 1 to 11 may be made from any suitable density polymer foam and/or latex material, by cutting the material to shape using conventional cutting equipment, machining facilities and raw material are available. In particular the pillow may be manufactured by cutting material to appropriate rectangular, triangular and trapezoid shapes to form the different sections of the pillow. Typically the rib support 11 is formed from one or more materials of suitable density such as expanded polymer and/or latex. For example a piece of expanded polymeric foam may be cut in the shape of a right-angled trapezium to form the rib support 11. A suitable density polymeric foam or latex sheet may then be cut to form the upper inclined surface 11. The sheet is typically slightly longer than the rib support 15 to allow for it folding over the upper edge of the right-angled trapezium. The sheet may then be aligned vertically and horizontally with the rib support 15 starting from a lower end 13 of the right angled trapezium and is then glued all the way to a top end 12 of the right-angled trapezium. The extra length of the sheet is then rolled over the edge of top end 12 of the right-angled trapezium and folded downwards and glued to an elevated front section 10 as well as to top surface 37 of the bridge 9.

The rolled over section of the sheet provides strength, support, comfort, flexibility, and generally maintains shape and minimizes sagging. The construction of the rib support 11 of the pillow is important because this section of the pillow carries the bulk of the weight of the body during sleep. It supports the body in a slight upward angle from the end of the spine, through the rib cage, to the shoulder and arm. The angle of inclined section 11 is lower than the angle of the upper surface 1 of the headrest 5. This difference in height is intentional because it compensates for the curvature from the shoulder to the neck while sleeping on either side. Projection 39 of headrest 5 fits neatly under the neck of the user and, together with the angle of headrest 5, provides alignment, posture and comfort for the head, neck, rib cage and spine.

Inflatable

In an alternate embodiment, as opposed to building a pillow from suitable expanded polymer or latex or similar solid material, the pillow may comprise one or more inflatable sections. The design, shape and configuration of the inflatable pillow may conform with the preferred embodiment described previously with reference to FIGS. 1 to 6.

Figure 12:
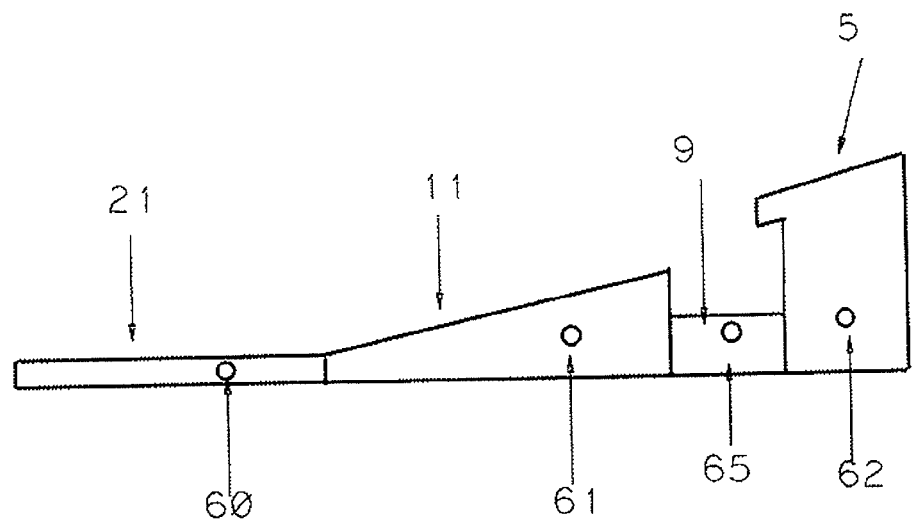
FIG. 12 illustrates, in right side view, an inflatable ergonomic support apparatus in accordance with a further embodiment.
Figure 13:
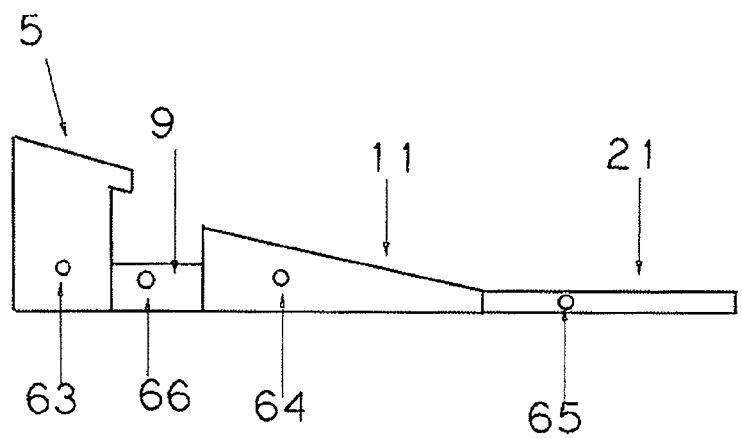
FIG. 13 illustrates, in left side view, the ergonomic support apparatus in accordance with the embodiment shown in FIG. 12.

FIGS. 12 and 13 are opposing side views illustrating an inflatable pillow, according to an embodiment of the present invention. The process of constructing the inflatable pillow will vary substantially from manufacture of the pillow from a solid material. Typically, the inflatable embodiment, the pillow or sections of pillow are engineered for structural stability and made from material that can be cut and welded together. Inflatable embodiments of the pillow may require suitable rib structures built within the pillow to allow for uniform blow up of air to maintain consistent flat surfaces on the top surface 1 of the headrest 5, the upper surface 11 of the rib support 11 and the cushion 21.

The inflatable pillow may have one or more valves. For example in one embodiment there could be eight valves—four inlet valves 60, 61, 67, and 62 on one side of the pillow for inflation, and four outlet valves 63, 66, 64, and 65, for deflation. Alternate inflatable embodiments may comprise various numbers of valves in different locations. The pillow may be inflated by any convenient means including, but not limited to, a hand pump or an electrical air pump.

Currently there are many pillows available in the global market for people with sleep apnea and snoring issues/problems. But many do not work for all people as they principally support the head and neck only. If sufficient care is not taken to ensure the head and spine are aligned for sleeping, then the airways may not be clear in some positions and the issues of sleep apnea and snoring may not be addressed.

Accordingly, the present invention is directed to providing a pillow that will overcome the problems discussed above. A pillow according to preferred embodiments of the present invention adopts a holistic approach to the body's need to be relaxed and stress free during rest or sleep. It is designed to assist sufferers to considerably reduce and/or eliminate the problem of snoring and sleep apnea.

In the light of the enormous variation in human anatomy, the conformation of the present invention can be optimised to improve a user's body posture during sleep and rest and ameliorate any conditions that may detract from sleep. For example the pillow of the present invention may assist by reducing snoring and breathing problems and ameliorate OSA by correcting the posture of the user during sleep. Without wishing to be bound by theory, the desired result may be achieved at least in part by the combination of the angle, structure and material used for headrest 5. When sleeping with the head resting on headrest 5, the foam or latex follows the contours of the head providing support and comfort. The user will experience the same comfort whether they lie on their left or right side or in the supine position. Maximum benefit is achieved while sleeping on the left or right side.

Entities that may be interested in the pillows according to embodiments of the present invention may comprise, without limitation, hospitals, chemist shops, health care products outlets, health and fitness businesses, medical centers, and the general public.

Pillows according to embodiments of the present invention are designed to meet the needs of people who suffer from poor quality sleep due to intrinsic or extrinsic factors and comprises those who suffer from snoring and sleep apnea problems. The pillow are designed to reduce and/or eliminate the problems by providing comfort, posture and alignment for the head, neck, arm, shoulder and spine. Embodiments may be provided to suit two basic groups of people, people who are light to medium weight and people who are medium to heavy weight. Suitable density foam and/or latex are used to compensate for the varying weight ratios of each group.

Preferred embodiments of the present invention are designed to give full support and elevation for the upper body to generally ensure the head, neck arm, shoulder and spine sections are aligned and have the proper posture during resting or sleeping. This is achieved by generally eliminating unwanted stress or pressure in the upper areas of the body and by providing the proper incline and suitable density foam or latex support. Embodiments of the present invention are uniquely designed to have the correct support for the head, neck, shoulder, arm, and the spine. These embodiments support the total upper body by providing a comfortable posture for the person trying to rest or sleep by allowing the head to be well cushioned and stress free at the elevated end or top end, while the arm and shoulder rests in the open recess section. This generally prevents any stress or pressure on the neck and spine section of the body while resting or sleeping on either side (left or right). Since the neck portion is also free from any weight or pressure as the head is freely resting on the headrest, this allows clear and casual breathing thereby minimizing or eliminating any sleep or snoring issues/problems.

While this invention has been described in connection with specific embodiments thereof, it will be understood that it is capable of further modification(s). This application is intended to cover any variations uses or adaptations of the invention following in general, the principles of the invention and including such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. The described embodiments are to be considered in all respects as illustrative only and not restrictive.

Various modifications and equivalent arrangements are intended to be included within the spirit and scope of the invention and appended claims. Therefore, the specific embodiments are to be understood to be illustrative of the many ways in which the principles of the present invention may be practiced. In the following claims, means-plus-function clauses are intended to cover structures as performing the defined function and not only structural equivalents, but also equivalent structures. For example, although a nail and a screw may not be structural equivalents in that a nail employs a cylindrical surface to secure wooden parts together, whereas a screw employs a helical surface to secure wooden parts together, in the environment of fastening wooden parts, a nail and a screw are equivalent structures.

"Comprises/comprising" and "includes/including" when used in this specification is taken to specify the presence of stated features, integers, steps or components but does not preclude the presence or addition of one or more other features, integers, steps, components or groups thereof. Thus, unless the context clearly requires otherwise, throughout the description and the claims, the words 'comprise', 'comprising', 'include', 'including' and the like are to be construed in an inclusive sense as opposed to an exclusive or exhaustive sense; that is to say, in the sense of "including, but not limited to".

The invention claimed is:

1. A postural support apparatus for use on a horizontal surface to support an upper body of a user, the postural support comprising:
   a first support configured to be supported by the horizontal surface, said first support having a first top surface configured to support a head of the user above the horizontal surface;
   a second support configured to be supported by the horizontal surface, said second support spaced from said first support, said second support comprising a second top surface configured to support and incline a rib cage of the user relative to the horizontal surface while leaving legs of the user to rest substantially horizontal on the horizontal surface, said second top surface disposed at an angle extending upwardly from the horizontal surface such that a first end of the second top surface, proximal the first support, extends from the horizontal surface a greater distance than a second end of the second top surface extends from the horizontal surface, the second end being distal from the first support and associated with an end of a spine of the user;
   a bridge configured to be supported by the horizontal surface, said bridge positioned intermediate the first support and second support, the bridge having a third top surface defining a bottom portion of a channel disposed between and separating the first support and the second support, said channel being of a size to accommodate at least part of an arm of the user; and
   bridge extensions laterally projectable outwards from said bridge to provide additional support to the user's arms;
   wherein the channel is configured to store the bridge extensions and is shaped so as to provide the same comfort whether the user lies on a left side or a right side of the upper body of the user;
   wherein said bridge extensions are hingedly attached to said bridge so as to pivot for storage in said channel;
   wherein the first support and the second support are configured and disposed to align the head and spine of the user whereby the user's airways are kept open;
   wherein said first top surface of said first support is disposed at a higher elevation than said second top surface of said second support; and wherein said first top surface of said first support overhangs said channel at a position to fit under the neck of the user.

2. The apparatus of claim 1 wherein said first support includes an edge portion which overhangs said channel.

3. The apparatus of claim 2 wherein said edge portion includes a rounded edge.

4. The apparatus of claim 1 wherein said first support has an upper section and a lower section, said upper section being detachably mounted to said lower section.

5. The apparatus of claim 4 further comprising at least one insert receivably mountable between said upper section and said lower section.

6. The apparatus of claim 1 wherein said first support has an upper section and a lower section, said upper section formed of a low density material and said lower section formed of a high density material.

7. A postural support apparatus for use on a horizontal surface to support an upper body of a user, the postural support comprising:
 a first support having a first top surface configured to support a head of the user;
 a second support spaced from said first support and configured to support and incline a rib cage of the user relative to the horizontal surface, said second support having a second top surface adapted to be disposed at an angle extending upwardly beginning from an end of a spine of the user and toward the head of the user while leaving legs of the user to rest substantially horizontal on the horizontal surface;
 a bridge positioned intermediate the first support and second support, the bridge having a third top surface defining a bottom portion of a channel disposed between and separating the first support and the second support; and
 bridge extensions laterally projectable outwards from said bridge to provide additional support to the user's arms;
 wherein said channel is sized to accommodate at least part of an arm of the user and to store the bridge extensions; and
 wherein said bridge extensions are hingedly attached to said bridge so as to pivot for storage in said channel.

8. The apparatus of claim 7, wherein said first top surface of said first support is disposed at a higher elevation than said second top surface of said second support.

9. The apparatus of claim 7, wherein said first top surface of said first support overhangs said channel.

* * * * *